United States Patent
Carpentier et al.

(10) Patent No.: US 9,371,418 B2
(45) Date of Patent: *Jun. 21, 2016

(54) METHOD OF COPOLYMERIZING ETHYLENE CARBONATE WITH ONE OR MORE CYCLIC ESTERS

(71) Applicants: TOTAL RESEARCH & TECHNOLOGY FELUY, Seneffe (BE); CENTRE NATIONAL DE LA RECHERCHE SCIENTIFIQUE, Paris (FR)

(72) Inventors: Jean-François Carpentier, Acigne (FR); Sophie Guillaume, Vitre (FR); William Guerin, Rennes (FR)

(73) Assignees: Total Research & Technology Feluy, Seneffe (BE); Centre National de la Recherche, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/407,834

(22) PCT Filed: Jun. 13, 2013

(86) PCT No.: PCT/EP2013/062276
§ 371 (c)(1),
(2) Date: Dec. 12, 2014

(87) PCT Pub. No.: WO2013/186313
PCT Pub. Date: Dec. 19, 2013

(65) Prior Publication Data
US 2015/0166722 A1    Jun. 18, 2015

(30) Foreign Application Priority Data
Jun. 15, 2012 (EP) ..................................... 12290198

(51) Int. Cl.
| | | |
|---|---|---|
| *C08G 63/64* | (2006.01) | |
| *C08G 63/08* | (2006.01) | |
| *C08G 63/82* | (2006.01) | |
| *C08G 63/83* | (2006.01) | |
| *C07D 317/36* | (2006.01) | |
| *C08G 64/18* | (2006.01) | |

(52) U.S. Cl.
CPC ................ C08G 63/64 (2013.01); C08G 63/08 (2013.01); C08G 63/823 (2013.01); C08G 63/83 (2013.01); *C07D 317/36* (2013.01); *C08G 64/18* (2013.01)

(58) Field of Classification Search
CPC ........ C08G 63/08; C08G 64/18; C08G 63/64; C08G 63/83; C08G 63/82; C07D 317/36
See application file for complete search history.

(56) References Cited

U.S. PATENT DOCUMENTS

| | | |
|---|---|---|
| 2011/0077380 A1 | 3/2011 | Williams et al. |
| 2012/0101233 A1 | 4/2012 | Carpentier et al. |
| 2014/0148558 A1 * | 5/2014 | Helou .................... C08G 63/08 525/450 |

FOREIGN PATENT DOCUMENTS

WO    2012/038240 A1    3/2012

OTHER PUBLICATIONS

Lee J. C., Litt M. H.; Macromolecules, 2000, 33, 1618-1627.
Agarwal S., Naumann N., Xie X.; Macromolecules, 2002, 35, 7713-7717.
Chamberlain B. M., Cheng M., Moore D. R., Ovitt T. M., Lobkovsky E. B., Coates G. W.; J. Am; Chem. Soc., 2001, 123, 3229-3230.
Williams C. K., Breyfogle L. E., Choi S. K., Nam W., Young V. G., Hillmeyer M. A., Tolman W. B.; J. Am. Chem. Soc., 2003, 125, 11350-11359.
International Search Report issued in International Application No. PCT/EP2013/062276, dated Jul. 29, 2013 (2 pages).

* cited by examiner

*Primary Examiner* — Gregory Listvoyb
(74) *Attorney, Agent, or Firm* — Albert Shung

(57) ABSTRACT

A process for copolymerizing selectively i) ethylene carbonate with ii) one or more cyclic esters can include contacting the ethylene carbonate with the one or more cyclic esters in the presence of a catalyst. The catalyst can be a Zn-complex with a diaminophenolate ligand (NNO) or a β-diiminate ligand (BDI).

17 Claims, 9 Drawing Sheets

METHOD OF COPOLYMERIZING ETHYLENE CARBONATE WITH ONE OR MORE CYCLIC ESTERS

CROSS REFERENCE TO RELATED APPLICATIONS

This application is a national stage entry of PCT/EP2013/062276, filed on Jun. 13, 2013, which claims priority from European Application No. 12290198.6, filed on Jun. 15, 2012.

FIELD OF THE INVENTION

The present invention relates to a process for copolymerizing i) ethylene carbonate with ii) one or more cyclic esters, and polymers obtained therewith.

BACKGROUND OF THE INVENTION

In the past 2 decades, there has been considerable interest in aliphatic polycarbonates for widespread applications in medicine and pharmacy because of their high biocompatibility, facile biodegradation, low toxicity, and excellent mechanical properties.

The most convenient method for preparing polycarbonates with high molecular weights and narrow molecular weight distributions seems to be the ring-opening polymerization (ROP) of cyclic carbonates. However, ring-opening polymerization of five-membered cyclic carbonates like ethylene carbonate (EC) or propylene carbonate (PC) does not allow to obtain pure poly(ethylene carbonate) (PEC) and poly(propylene carbonate) (PPC) homopolymers. As such, during the last decades some groups have tried to copolymerize cyclic carbonates with cyclic esters.

It is very difficult for five-membered cyclic carbonates to co-polymerize, or to ring-open without undergoing undesirable decarboxylation side reactions, or to react without degradation, or without producing un-recoverable copolymers, only to name a few of the problems involved. In addition, the selection of the catalyst can be critical. Catalytic systems based on tin, aluminum, rare earth metals, magnesium or calcium are known as catalysts for the ring-opening polymerization of cyclic carbonates. However, some of these catalysts are possibly toxic or at least possibly involve toxic reagents during the polymerization process, which makes these unsuitable for producing pharmaceutical grade aliphatic polycarbonates. Also, some of these catalysts are very sensitive to protic impurities and are not well suited for large scale industrial applications.

There is therefore a need for improved and effectively workable processes of copolymerization of cyclic carbonates.

Consequently, it is an object of the present invention to provide an improved process for the effective copolymerization of ethylene carbonate It is also an objective of the present invention to prepare fully bio resourced polycarbonate/polyester copolymer

SUMMARY OF THE INVENTION

The present inventors have now found that this object can be obtained by using a process for the copolymerization of ethylene carbonate with cyclic esters as presently claimed.

In particular, the present invention relates to a process for copolymerizing i) ethylene carbonate with ii) one or more cyclic esters, comprising contacting the ethylene carbonate with the one or more cyclic esters in the presence of one or more catalysts such as those of formula (I) or (II),

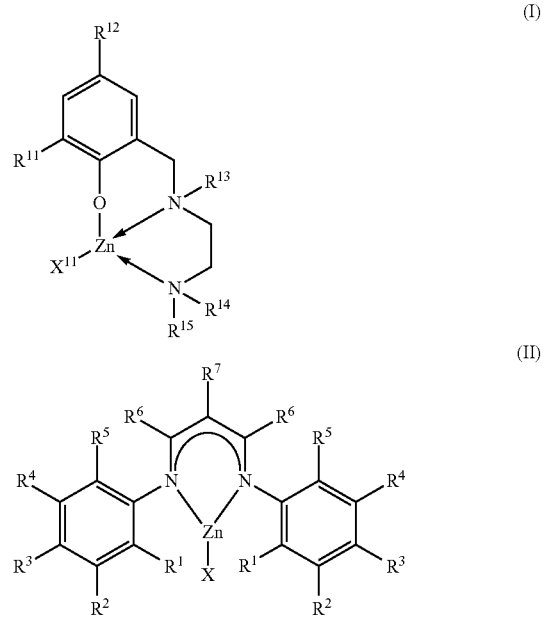

wherein
$R^1, R^2, R^3, R^4, R^5, R^6$, and $R^7$ are each independently selected from the group consisting of hydrogen, optionally substituted $C_{1-12}$ alkyl, and an inert functional group (e.g., —CN), and wherein two or more of said groups can be linked together to form one or more rings,
X is —N(SiR$^{27}_3$)$_2$, $C_{1-12}$alkyl, $C_{1-12}$alkoxy, —NR$^9$R$^{10}$ or —BH$_4$,
each $R^{27}$ is independently selected from hydrogen and $C_{1-6}$alkyl;
each $R^9$ and $R^{10}$ is independently selected from hydrogen and $C_{1-6}$alkyl;
$R^{11}$ and $R^{12}$ are each independently $C_{1-10}$alkyl,
$R^{13}$, $R^{14}$, and $R^{15}$ are each independently $C_{1-10}$alkyl, or $R^{13}$ and $R^{14}$ are covalently bound to each other and are each a methylene and $R^{15}$ is $C_{1-10}$alkyl,
$X^{11}$ is selected from $C_{1-10}$alkyl, —OR$^{16}$, and —N(SiR$^{17}_3$)$_2$,
$R^{16}$ is $C_{1-10}$alkyl, and
wherein each $R^{17}$ is selected from hydrogen and $C_{1-6}$alkyl.

The process of the present invention allows copolymerizing ethylene carbonate with cyclic esters such as β-butyrolactone, δ-valerolactone, ε-caprolactone, or lactide, by using zinc-based catalytic systems. As such, the present invention provides a method of incorporating selectively ethylene carbonate units or segments into a polyester material, thereby allowing the preparation of bioresourced polycarbonate/polyester copolymers.

The process of the present invention affords a larger content of inserted carbonate units into the poly(lactone) or poly(lactide) than ever reported, which content may be tuned as it may be required.

Furthermore, the process of the present invention allows the production of polycarbonates/polyester copolymers with improved properties such as high molecular mass and narrow molecular mass distribution in an efficient and hence economical way. Further, in some embodiments, the process of the present invention allows the preparation of polycarbonate/polyester copolymers in a one-pot and one-step method.

In addition, the process of the present invention allows modulation of the thermal and physical properties of a polyester such as polylactide upon introducing ethylene carbonate units or segments.

The present invention therefore also encompasses a process for the preparation of polycarbonate/polyester copolymers comprising the step of contacting ethylene carbonate with the one or more cyclic esters in the presence of one or more catalysts of formula (I) or (II), as described herein.

The independent and dependent claims set out particular and preferred features of the invention. Features from the dependent claims may be combined with features of the independent or other dependent claims as appropriate.

The above and other characteristics, features and advantages of the present invention will become apparent from the following detailed description, taken in conjunction with the accompanying drawings, which illustrate, by way of example, the principles of the invention. The reference figures quoted below refer to the attached drawings.

DETAILED DESCRIPTION OF THE INVENTION

Figure 1:
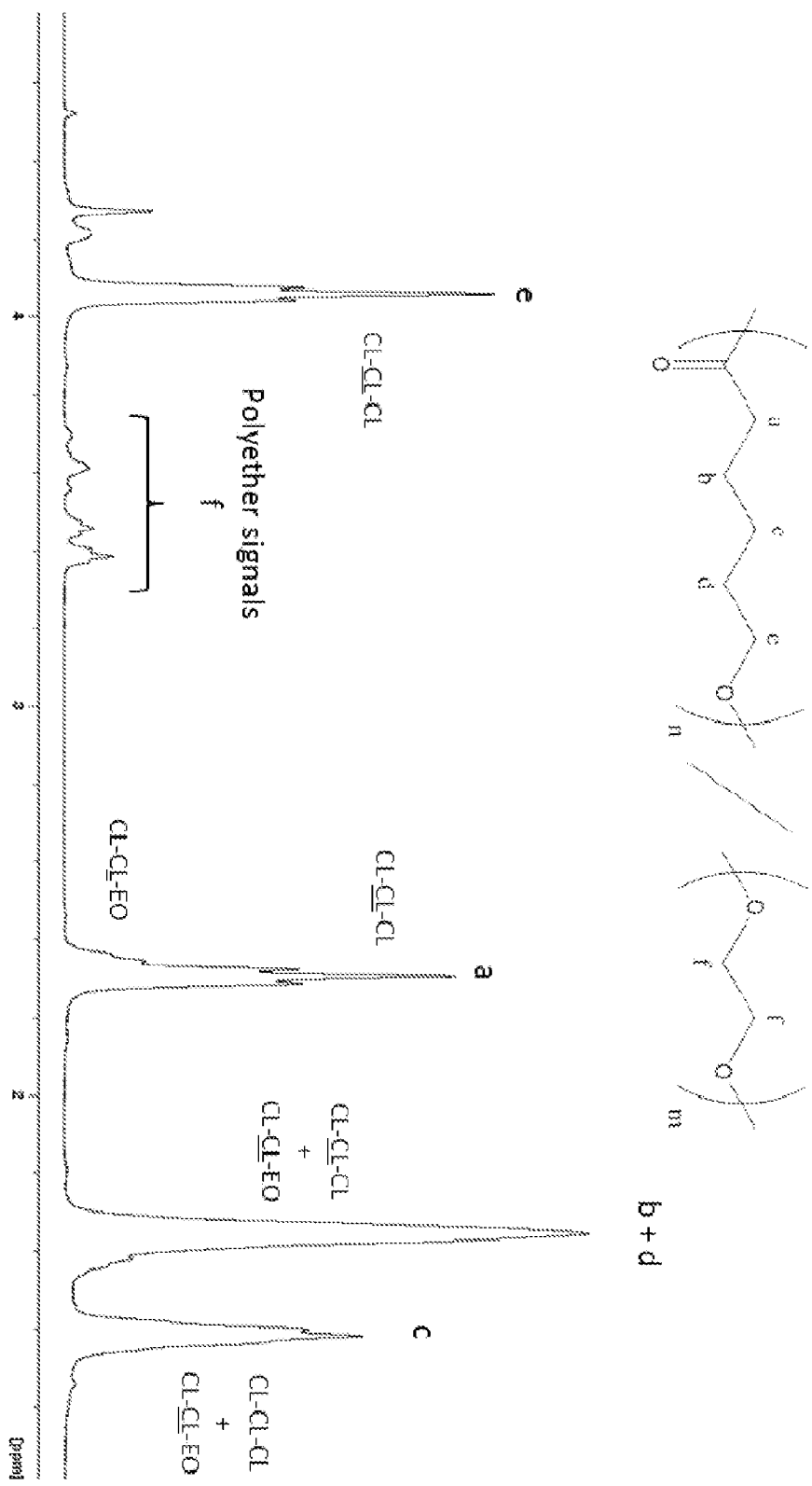
FIG. 1 illustrates the $^1$H NMR spectrum (CDCl$_3$, 400 MHz, 23° C.) of the polymer recovered from the copolymerization of EC and ε-caprolactone (CL) (Table 1, entry 1) and relating to comparative Example 1.

Before the present process of the invention is described, it is to be understood that this invention is not limited to particular processes, components, or devices described, as such processes, components, and devices may, of course, vary. It is also to be understood that the terminology used herein is not intended to be limiting, since the scope of the present invention will be limited only by the appended claims.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. The terms "comprising", "comprises" and "comprised of" also include the term "consisting of".

The recitation of numerical ranges by endpoints includes all numbers and fractions subsumed within the respective ranges, as well as the recited endpoints.

The term "about" as used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" refers is itself also specifically, and preferably, disclosed.

Unless otherwise defined, all terms used in disclosing the invention, including technical and scientific terms, have the meaning as commonly understood by one of ordinary skill in the art to which this invention belongs. By means of further guidance, definitions for the terms used in the description are included to better appreciate the teaching of the present invention.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

When describing the present invention, the terms used are to be construed in accordance with the following definitions, unless a context dictates otherwise.

Whenever the term "substituted" is used in the present invention, it is meant to indicate that one or more hydrogens on the atom indicated in the expression using "substituted" is replaced with a selection from the indicated group, provided that the indicated atom's normal valency is not exceeded, and that the substitution results in a chemically stable compound, i.e. a compound that is sufficiently robust to survive isolation to a useful degree of purity from a reaction mixture.

The term "$C_{1-20}$alkyl", as a group or part of a group, refers to a hydrocarbyl radical of formula $C_nH_{2n+1}$ (or $C_nH_{2n-1}$ for a cyclic one) wherein n is a number ranging from 1 to 20, for linear or branched alkyl and n is a number ranging from 3 to 20 for cycloalkyl. Generally, the alkyl groups comprise from 1 to 20 carbon atoms, preferably from 3 to 12 carbon atoms, more preferably 3, 4, 5, 6, 7, 8, 9, 10, 11 or 12 carbon atoms. Alkyl groups may be linear, branched or cyclic and may be substituted as indicated herein. When a subscript is used herein following a carbon atom, the subscript refers to the number of carbon atoms that the named group may contain.

Thus, for example, $C_{1-20}$alkyl groups include all linear, branched or cyclic alkyl groups with between 1 and 20 carbon atoms, and thus includes for example methyl, ethyl, cyclopropyl, n-propyl, i-propyl, 2-methyl-ethyl, cyclobutyl, butyl and its isomers (e.g. n-butyl, i-butyl and t-butyl); cyclopentyl, pentyl and its isomers, cyclohexyl, hexyl and its isomers, cycloheptyl, heptyl and its isomers, cyclooctyl, octyl and its isomers, nonyl and its isomers, decyl and its isomers, undecyl and its isomers, dodecyl and its isomers, tridecyl and its isomers, tetradecyl and its isomers, pentadecyl and its isomers, hexadecyl and its isomers, heptadecyl and its isomers, octadecyl and its isomers, nonadecyl and its isomers, icosyl and its isomers, and the like. For example, $C_{1-10}$alkyl includes all linear, or branched or cyclic alkyl groups with between 1 and 10 carbon atoms, and thus includes for example methyl, ethyl, n-propyl, i-propyl, 2-methyl-ethyl, butyl and its isomers (e.g. n-butyl, i-butyl and t-butyl); pentyl and its isomers, hexyl and its isomers, heptyl and its isomers, octyl and its isomers, nonyl and its isomers, decyl and its isomers and the like. For example, $C_{1-6}$alkyl includes all linear, or branched or cyclic alkyl groups with between 1 and 6 carbon atoms or with between 3 to 6 carbon for cycloalkyl, and thus includes for example methyl, ethyl, n-propyl, i-propyl, 2-methyl-ethyl, butyl and its isomers (e.g. n-butyl, i-butyl and t-butyl); pentyl and its isomers, hexyl and its isomers.

The term "$C_{6-30}$aryl", as a group or part of a group, refers to a polyunsaturated, aromatic hydrocarbyl group having a single ring (i.e. phenyl) or multiple aromatic rings fused together (e.g. naphthalene), or linked covalently, typically containing 6 to 30 atoms; wherein at least one ring is aromatic. Non-limiting examples of $C_{6-30}$aryl comprise phenyl, biphenylyl, biphenylenyl, or 1- or 2-naphthalenyl. Examples of suitable aryl include $C_{6-12}$aryl, more preferably $C_{6-10}$aryl. Non-limiting examples of $C_{6-12}$aryl comprise phenyl, biphenylyl, biphenylenyl, or 1- or 2-naphthanelyl.

The term "$C_{6-30}$aryl$C_{1-20}$alkyl", as a group or part of a group, means a $C_{1-20}$alkyl as defined herein, wherein a hydrogen atom is replaced by a $C_{6-30}$aryl as defined herein. Preferred $C_{6-30}$aryl$C_{1-20}$alkyl includes $C_{6-12}$aryl$C_{1-6}$alkyl. Non-limiting examples of $C_{6-12}$aryl$C_{1-6}$alkyl group include benzyl, phenethyl, dibenzylmethyl, methylphenylmethyl, 3-(2-naphthyl)-butyl, and the like.

The term "halogen", as a group or part of a group, is generic for fluoro, chloro, bromo or iodo.

The present invention provides a process for copolymerizing i) ethylene carbonate with ii) one or more cyclic esters, comprising contacting the ethylene carbonate with the one or more cyclic esters in the presence of a catalyst of formula (I) or (II),

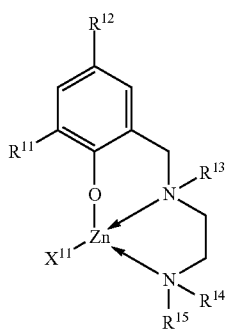

(I)

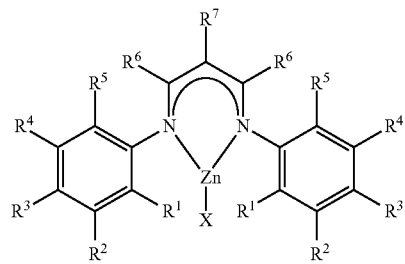

(II)

wherein
$R^1, R^2, R^3, R^4, R^5, R^6$, and $R^7$ are each independently selected from the group consisting of hydrogen, optionally substituted $C_{1-12}$alkyl, and an inert functional group (e.g., CN), and wherein two or more of said groups can be linked together to form one or more rings, preferably $R^1, R^2, R^3, R^4, R^5, R^6$, and $R^7$ are each independently selected from the group consisting of hydrogen, optionally substituted $C_{1-8}$alkyl, and an inert functional group (e.g., CN), and wherein two or more of said groups can be linked together to form one or more rings, preferably $R^1, R^2, R^3, R^4, R^5, R^6$, and $R^7$ are each independently selected from the group consisting of hydrogen, optionally substituted $C_{1-8}$alkyl, and an inert functional group (e.g., CN), and wherein two or more of said groups can be linked together to form one or more rings; preferably $R^1, R^2, R^3, R^4, R^5, R^6$, and $R^7$ are each independently selected from the group consisting of hydrogen, or optionally substituted $C_{1-6}$alkyl, preferably $R^1, R^2, R^3, R^4, R^5, R^6$, and $R^7$ are each independently selected from the group consisting of hydrogen, or optionally substituted $C_{1-4}$alkyl, preferably $R^2, R^3, R^4$ and $R^7$ are each independently H, and $R^1, R^5$, and $R^6$, are each independently $C_{1-6}$alkyl, X is $-N(SiR^{27}_3)_2$, $C_{1-12}$alkyl, $C_{1-12}$alkoxy, $-NR^9R^{10}$ or $-BH_4$, preferably X is $-N(SiR^{27}_3)_2$, $C_{1-6}$alkyl, $C_{1-6}$alkoxy, or $-NR^9R^{10}$, preferably X is $-N(SiR^{27}_3)_2$, $C_{1-6}$alkyl, $C_{1-6}$alkoxy, or $-NR^9R^{10}$; preferably X is $-N(SiR^{27}_3)_2$, and each $R^9$ and $R^{10}$ is independently selected from hydrogen and $C_{1-6}$alkyl;

each $R^{27}$ is independently selected from hydrogen and $C_{1-6}$alkyl;

$R^{11}$ and $R^{12}$ are each independently $C_{1-10}$alkyl; preferably, $R^{11}$ and $R^{12}$ are each independently $C_{1-6}$alkyl; preferably, $R^{11}$ and $R^{12}$ are each independently $C_{1-4}$alkyl; for example, $R^{11}$ and $R^{12}$ can be each independently selected from the group consisting of methyl, ethyl, n-propyl, i-propyl, 2-methyl-ethyl, n-butyl, i-butyl and t-butyl; preferably, $R^{11}$ and $R^{12}$ can be each independently selected from the group consisting of methyl, ethyl, i-propyl and t-butyl; for example $R^{11}$ and $R^{12}$ can be each independently selected from i-propyl or t-butyl; preferably, $R^{11}$ and $R^{12}$ are t-butyl, $R^{13}, R^{14}$ and $R^{15}$ are each independently $C_{1-10}$alkyl, preferably, $R^{13}, R^{14}$ and $R^{15}$ are each independently $C_{1-6}$alkyl, preferably $R^{13}, R^{14}$ and $R^{15}$ are each independently $C_{1-4}$alkyl, for example, $R^{13}, R^{14}$ and $R^{15}$ can be each independently selected from the group consisting of methyl, ethyl, n-propyl, i-propyl, 2-methyl-ethyl, n-butyl, i-butyl and t-butyl; for example, $R^{13}, R^{14}$ and $R^{15}$ can be each independently selected from the group consisting of methyl, ethyl, i-propyl and t-butyl; for example, $R^{13}, R^{14}$ and $R^{15}$ are each independently selected from methyl or ethyl; preferably, $R^{13}, R^{14}$ and $R^{15}$ are each independently methyl, or $R^{13}$ and $R^{14}$ are covalently bound to each other and are each a methylene and $R^{15}$ is $C_{1-10}$alkyl; preferably $R^{15}$ is $C_{1-6}$alkyl; preferably, $R^{15}$ is $C_{1-4}$alkyl; for example $R^{15}$ can be selected from the group consisting of methyl, ethyl, n-propyl, i-propyl, 2-methyl-ethyl, n-butyl, i-butyl and t-butyl; for example $R^{15}$ can be selected from the group consisting of methyl, ethyl, i-propyl and t-butyl; for example $R^{15}$ can be selected from methyl or ethyl; for example $R^{15}$ can be methyl;

$X^{11}$ is selected from $C_{1-10}$alkyl, $-OR^{16}$, or $-N(SiR^{17}{}_3)_2$, $R^{16}$ is $C_{1-10}$alkyl, and $R^{17}$ is $C_{1-6}$alkyl; preferably, $X^{11}$ is selected from $C_{1-6}$alkyl, $-OR^{16}$, or $-N(SiR^{17}{}_3)_2$, $R^{16}$ is $C_{1-6}$alkyl, and each $R^{17}$ is independently selected from hydrogen and $C_{1-6}$alkyl; preferably, $X^{11}$ is selected from $C_{1-4}$alkyl, $-OR^{16}$, or $-N(SiR^{17}{}_3)_2$, $R^{16}$ is $C_{1-4}$alkyl, and each $R^{17}$ is independently hydrogen or $C_{1-4}$alkyl; for example $X^{11}$ can be selected from the group consisting of methyl, ethyl, n-propyl, i-propyl, 2-methyl-ethyl, n-butyl, i-butyl and t-butyl, or $-OR^{16}$, or $-N(SiR^{17}{}_3)_2$, $R^{16}$ can be selected from the group consisting of methyl, ethyl, n-propyl, i-propyl, 2-methyl-ethyl, n-butyl, i-butyl and t-butyl, and each $R^{17}$ can be independently selected from the group consisting of hydrogen, methyl, ethyl, n-propyl, i-propyl, 2-methyl-ethyl, n-butyl, i-butyl and t-butyl; preferably, $X^{11}$ can be selected from the group consisting of methyl, ethyl, i-propyl and n-butyl, or $-OR^{16}$, $R^{16}$ can be selected from the group consisting of methyl, ethyl, i-propyl and t-butyl; preferably, $X^{11}$ can be selected from $-OR^{16}$, $R^{16}$ can be selected from the group consisting of methyl, ethyl, i-propyl and t-butyl; preferably, $X^{11}$ can be $-OR^{16}$, and $R^{16}$ is ethyl.

In the present description, an inert functional group is defined as a group containing one or several heteroatoms selected from O, N, S or halogen, that is(are) not reactive in the polymerization system neither as an initiating species nor as a chain transfer agent.

In an embodiment, the invention relates to a process for copolymerizing i) ethylene carbonate with ii) one or more cyclic esters, comprising contacting the ethylene carbonate with the one or more cyclic esters in the presence of a catalyst of formula (I), wherein $R^{11}$ and $R^{12}$ are each independently $C_{1-6}$alkyl. Preferably $R^{11}$ and $R^{12}$ are each independently $C_{1-4}$alkyl. Preferably, $R^{11}$ and $R^{12}$ can be each independently selected from the group consisting of methyl, ethyl, i-propyl and t-butyl; for example $R^{11}$ and $R^{12}$ can be each independently selected from i-propyl or t-butyl; preferably, $R^{11}$ and $R^{12}$ are t-butyl.

In an embodiment, the invention relates to a process for copolymerizing i) ethylene carbonate with ii) one or more cyclic esters, comprising contacting the ethylene carbonate with the one or more cyclic esters in the presence of a catalyst of formula (I), wherein $R^{13}$, $R^{14}$ and $R^{15}$ are each independently $C_{1-6}$alkyl. Preferably $R^{13}$, $R^{14}$ and $R^{15}$ are each independently $C_{1-4}$alkyl. For example, $R^{13}$, $R^{14}$ and $R^{15}$ can be each independently selected from the group consisting of methyl, ethyl, i-propyl and t-butyl; preferably, $R^{13}$, $R^{14}$ and $R^{15}$ can be each independently selected from methyl or ethyl; more preferably, $R^{13}$, $R^{14}$ and $R^{15}$ can be methyl.

In an embodiment, the invention relates to a process for copolymerizing i) ethylene carbonate with ii) one or more cyclic esters, comprising contacting the ethylene carbonate with the one or more cyclic esters in the presence of a catalyst of formula (I), wherein $R^{11}$ and $R^{12}$ are each independently $C_{1-6}$alkyl, and wherein $R^{13}$, $R^{14}$ and $R^{15}$ are each independently $C_{1-6}$alkyl. Preferably $R^{13}$, $R^{14}$ and $R^{15}$ are each independently $C_{1-4}$alkyl.

In an embodiment, the invention relates to a process for copolymerizing i) ethylene carbonate with ii) one or more cyclic esters, comprising contacting the ethylene carbonate with the one or more cyclic esters in the presence of a catalyst of formula (I), wherein $X^{11}$ is selected from $C_{1-6}$alkyl, $-OR^{16}$, or $-N(SiR^{17}{}_3)_2$, $R^{16}$ is $C_{1-6}$alkyl, and each $R^{17}$ is independently selected from hydrogen and $C_{1-4}$alkyl.

In an embodiment, the invention relates to a process for copolymerizing i) ethylene carbonate with ii) one or more cyclic esters, comprising contacting the ethylene carbonate with the one or more cyclic esters in the presence of a catalyst of formula (I), wherein $R^{11}$ and $R^{12}$ are each independently $C_{1-6}$alkyl, wherein $R^{13}$, $R^{14}$ and $R^{15}$ are each independently $C_{1-6}$alkyl, and wherein $X^{11}$ is selected from $C_{1-6}$alkyl, $-OR^{16}$, or $-N(SiR^{17}{}_3)_2$, $R^{16}$ is $C_{1-6}$alkyl, and each $R^{17}$ is independently selected from hydrogen and $C_{1-4}$alkyl.

In an embodiment, the invention relates to a process for copolymerizing i) ethylene carbonate with ii) one or more cyclic esters, comprising contacting the ethylene carbonate with the one or more cyclic esters in the presence of a catalyst of formula (I), wherein $R^{13}$, $R^{14}$ and $R^{15}$ are each independently $C_{1-6}$alkyl, and wherein $X^{11}$ is selected from $C_{1-6}$alkyl, $-OR^{16}$, or $-N(SiR^{17}{}_3)_2$, $R^{16}$ is $C_{1-6}$alkyl, and each $R^{17}$ is independently selected from hydrogen and $C_{1-4}$alkyl.

In an embodiment, the invention relates to a process for copolymerizing i) ethylene carbonate with ii) one or more cyclic esters, comprising contacting the ethylene carbonate with the one or more cyclic esters in the presence of a catalyst of formula (I), wherein $R^{11}$ and $R^{12}$ are each independently $C_{1-6}$alkyl, and wherein $X^{11}$ is selected from $C_{1-6}$alkyl, $-OR^{16}$, or $-N(SiR^{17}{}_3)_2$, $R^{16}$ is $C_{1-6}$alkyl, and each $R^{17}$ is independently selected from hydrogen and $C_{1-4}$alkyl.

For example, the process can be performed with a catalyst of Formula (I) wherein, $R^{11}$ and $R^{12}$ are each independently $C_{1-6}$alkyl; $R^{13}$ and $R^{14}$ are covalently bound to each other and are each a methylene and $R^{15}$ is $C_{1-6}$alkyl; and $X^{11}$ is selected from $C_{1-6}$alkyl, $-OR^{16}$, or $-N(SiR^{17}{}_3)_2$, $R^{16}$ is $C_{1-6}$alkyl, and each $R^{17}$ is independently selected from hydrogen and $C_{1-6}$alkyl.

For example, the process can be performed with a catalyst of Formula (I) wherein, $R^{11}$ and $R^{12}$ are each independently $C_{1-4}$alkyl; $R^{13}$, $R^{14}$ and $R^{15}$ are each independently $C_{1-4}$alkyl, $X^{11}$ is selected from $C_{1-4}$alkyl, $-OR^{16}$, or $-N(SiR^{17}{}_3)_2$, $R^{16}$ is $C_{1-4}$alkyl, and each $R^{17}$ is independently selected from hydrogen and $C_{1-4}$alkyl.

For example, the process can be performed with a catalyst of Formula (I) wherein, $R^{11}$ and $R^{12}$ are each independently $C_{1-4}$alkyl; $R^{13}$ and $R^{14}$ are covalently bound to each other and are each a methylene and $R^{15}$ is $C_{1-14}$alkyl; and $X^{11}$ is selected from $C_{1-4}$alkyl, $-OR^{16}$, or $-N(SiR^{17}{}_3)_2$, $R^{17}$ is $C_{1-4}$alkyl, and each $R^{17}$ is independently selected from hydrogen and $C_{1-4}$alkyl.

In a preferred embodiment, $R^{11}$ and $R^{12}$ are each independently $C_{1-4}$alkyl, preferably t-butyl or isopropyl; $R^{13}$, $R^{14}$ and $R^{15}$ are each independently $C_{1-2}$alkyl, $X^{11}$ is $-OR^{16}$, and $R^{15}$ is $C_{1-2}$alkyl.

In a preferred embodiment, $R^{11}$ and $R^{12}$ are each independently $C_{1-4}$alkyl, preferably t-butyl or isopropyl; $R^{13}$ and $R^{14}$ are covalently bound to each other and are each a methylene and $R^{14}$ is $C_{1-2}$alkyl; $X^{11}$ is $-OR^{16}$, $R^{16}$ is $C_{1-2}$alkyl.

In an embodiment, the invention relates to a process for copolymerizing i) ethylene carbonate with ii) one or more cyclic esters, comprising contacting the ethylene carbonate with the one or more cyclic esters in the presence of a catalyst selected from [(NNO)ZnEt], [BDI]Zn(N(SiMe$_3$)$_2$), [BDI]Zn(Et) and {[BDI]Zn(OR$^{30}$)}$_2$, wherein $R^{30}$ is $C_{1-6}$alkyl.

In an embodiment, the catalyst is selected from [(NNO)ZnEt], [BDI]Zn(N(SiMe$_3$)$_2$), [BDI]Zn(Et) and {[BDI]Zn(OR$^{30}$)}$_2$, wherein $R^{30}$ is $C_{1-6}$alkyl; preferably [(NNO)ZnEt].

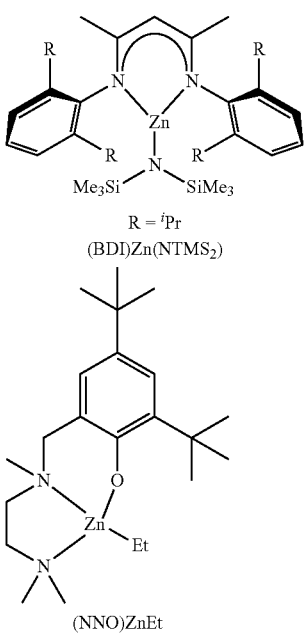

(BDI)Zn(NTMS₂)

(NNO)ZnEt

In an embodiment, the process can be performed in the presence of a co-initiator of the polymerization.

In an embodiment, the process is performed in the presence of a compound of formula (III), acting as a co-initiator and transfer agent of the polymerization, $$R^8\text{—OH} \qquad (III)$$

wherein $R^8$ is selected from the group consisting of $C_{1-20}$alkyl, $C_{6-30}$aryl, and $C_{6-30}$aryl$C_{1-20}$alkyl optionally substituted by one or more substituents selected from the group consisting of halogen, hydroxyl, and $C_{1-6}$alkyl. Preferably, $R^8$ is selected from $C_{3-12}$alkyl, $C_{6-10}$aryl, and $C_{6-10}$aryl$C_{3-12}$alkyl, optionally substituted by one or more substituents, each independently selected from the group consisting of halogen, hydroxyl, and $C_{1-6}$alkyl; preferably, $R^8$ is selected from $C_{3-12}$alkyl, $C_{6-10}$aryl, and $C_{6-10}$aryl$C_{3-12}$alkyl, optionally substituted by one or more substituents, each independently selected from the group consisting of halogen, hydroxyl and $C_{1-4}$alkyl. The alcohol can be a polyol such as diol, triol or higher functionality polyhydric alcohol. The alcohol may be derived from biomass such as for instance glycerol or 1,3-propanediol or any other sugar-based alcohol such as for example erythritol. The alcohol can be used alone or in combination with another alcohol.

In an embodiment, the invention relates to a process for copolymerizing i) ethylene carbonate with ii) one or more cyclic esters, comprising contacting the ethylene carbonate with the one or more cyclic esters in the presence of a catalyst selected from [(NNO)ZnEt], [BDI]Zn(N(SiMe₃)₂), [BDI]Zn(Et) and {[BDI]Zn(OR³⁰)}₂, wherein $R^{30}$ is $C_{1-6}$alkyl, and optionally in the presence of a compound of formula (III).

In an embodiment, non-limiting examples of initiators of formula (III) can be selected from the group comprising 1-octanol, isopropanol, propanediol, trimethylolpropane, 2-butanol, 3-buten-2-ol, 1,3-butanediol, 1,4-butanediol, 1,6-hexanediol, 1,7-heptanediol, benzyl alcohol, 4-bromophenol, 1,4-benzenedimethanol, and (4-trifluoromethyl)benzyl alcohol; preferably, said compound of formula (III) is selected from 1-octanol, isopropanol, and 1,4-butanediol.

The molar ratio of the co-initiator of formula (III) to the catalyst can be at least 0. For example, the molar ratio of the co-initiator of formula (III) to the catalyst can be of from about 0 to about 1000, for example from about 1 to about 1000, for example of from about 1 to about 100, for example of from about 10 to about 100.

As used herein, the terms "cyclic ester" refers to cyclic monoesters, cyclic diesters, cyclic triesters, and the like. Preferred are the cyclic monoesters also known as lactones, and the cyclic diesters also known as glycolide and lactides.

Non-limiting examples of suitable cyclic esters can be selected from the group comprising lactide, glycolide, β-butyrolactone, δ-valerolactone, γ-butyrolactone, γ-valerolactone, ε-caprolactone, and mixture thereof. In some embodiment, said cyclic ester is a lactide, such as L-lactide (S,S-lactide), D-lactide (R,R-lactide), or meso-(S,R)-lactide.

In an embodiment, the present invention relates to a process for copolymerizing i) ethylene carbonate with ii) one or more cyclic esters, comprising contacting the ethylene carbonate with the one or more cyclic esters in the presence of a catalyst of formula (I) or (II), possibly in the presence of co-initiator of formula $R^8$—OH, wherein the cyclic ester is selected from the group comprising glycolide (GL), lactide (LA), β-butyrolactone (BL), δ-valerolactone (VL), and ε-caprolactone (CL).

The copolymerization between the ethylene carbonate and the cyclic ester can occur with the same cyclic ester monomer or with two or more cyclic ester monomers.

In an embodiment, copolymerization of ethylene carbonate with one or more cyclic esters occurs by ring-opening polymerization.

In an embodiment, the ratio of the ethylene carbonate to β-butyrolactone to the catalyst can be from 165:500:1 to 250:500:1.

In an embodiment, the ratio of the ethylene carbonate to ε-caprolactone to the catalyst can be from 125:250:1, 250:250:1, to 500:250:1.

In an embodiment, the ratio of the ethylene carbonate to δ-valerolactone to the catalyst can be from 125:250:1, 250:250:1, to 500:250:1.

In an embodiment, the ratio of the ethylene carbonate to lactide to the catalyst can be from 500:100:1, 250:100:1, 150:150:1, to 100:250:1.

In an embodiment, the molar ratio of the ethylene carbonate to lactide can be from 83:17, 71:29, 50:50, to 29:71. Preferably the molar ratio of the ethylene carbonate to lactide is 83:17 or around 83:17.

In an embodiment, the process can be performed at a temperature of at least 60° C., preferably of at least 60° C. and at most 150° C., for example of at least 60° C. and at most 120° C., preferably of at least 80° C. and at most 120° C.; preferably of at least 80° C. and at most 100° C.

The process can be performed with or without solvent (in bulk), or can be performed in a minimum amount of solvent. In an embodiment, said minimum amount of solvent can be the solvent necessary to dissolve the catalyst. The solvent can be an aromatic or aliphatic hydrocarbon, an ether, or an halogenated solvent such as chlorinated solvent.

In an embodiment, the solvent is selected from an alkane such as hexane or heptane; an aromatic hydrocarbon such as toluene; an ether such as tetrahydrofuran (THF); and a chlorinated solvent such dichloromethane; preferably the solvent an aromatic hydrocarbon, such as toluene.

In an embodiment, the process can be performed in bulk, for instance the process can be performed in molten ethylene carbonate and molten cyclic esters.

In an embodiment, the copolymer prepared is an ether-free poly(ethylene carbonate)/polyester copolymer. In an embodiment, the process is carried out with no or minimal decarboxylation.

In an embodiment, the process can be carried out with unpurified ethylene carbonate and unpurified cyclic ester monomer. The process can also be carried out with the resulting copolymer being crystallized one or more times in solvent and dried under vacuum before use. The solvent used during crystallization can be the same or different from the solvent used during the polymerization process.

In an embodiment, the process can be performed by contacting said ethylene carbonate with the cyclic ester monomer with the catalyst and optionally the co-initiator, in a reactor equipped with an agitator, for instance a high viscosity agitator.

In an embodiment, the process can be performed by contacting ethylene carbonate, the cyclic ester, the catalyst, and optionally the co-initiator, under inert atmosphere, for example in the presence of argon or nitrogen.

In an embodiment, the process can be performed in the presence of stabilizing agents or antioxidants known by the skilled in the art. The stabilizing agent can be for instance (2,4-di-tert-butylphenyl)pentaerythritol diphosphite, also named Ultranox 626. The process can be performed in a continuous or discontinuous manner.

In an embodiment, the process is performed with a lactone selected from the group comprising β-butyrolactone, δ-valerolactone, and ε-caprolactone, and at a temperature of at least 60° C. In an embodiment, the process is performed with a lactone selected from the group comprising β-butyrolactone, δ-valerolactone, and ε-caprolactone, at a temperature of at most 110° C.

In an embodiment, the process is performed with a lactone selected from the group comprising β-butyrolactone, δ-valerolactone, and ε-caprolactone, in the presence of a solvent, and at a temperature of at least 60° C. and at most 110° C.

In an embodiment, the process is performed with a lactone selected from the group comprising β-butyrolactone (BL), δ-valerolactone (VL), and ε-caprolactone (CL), in bulk and at a temperature of at least 60° C. and at most 80° C.

In an embodiment, the process is performed with glycolide or a lactide and at a temperature of at least 60° C. In an embodiment, the process is performed with glycolide or a lactide and at a temperature of at most 120° C.

In an embodiment, the process is performed with glycolide or a lactide and at a temperature of at least 60° C. and at most 120° C., preferably at least 80° C. and at most 120° C., also preferably at least 80° C. and 100° C.

The present invention also encompasses polycarbonate/polyester copolymers obtainable by any one of the processes of the invention. In an embodiment, the invention relates to random copolymers obtainable by the process according to any one of the embodiments presented herein.

The inventors found that the copolymers prepared with the process of the invention have high molar mass and narrow molar mass distribution. The "mass distribution" or "molar mass distribution" is defined by the ratio $M_w/M_n$ of the weight average molecular weight $M_w$ to the number average molecular weight $M_n$ as determined by Size Exclusion Chromatography.

In an embodiment, the present process allows the preparation of copolymers, with a number average molecular weight $M_n$ which can range between about 4,000 and about 100,000 g·mol$^{-1}$. For example the $M_n$ of the copolymers obtained can range between about 6,000 and about 97,000 g·mol$^{-1}$. Specific $M_n$ values of the copolymers obtained are provided in the tables below.

The $M_n$ can be measured by any adequate technique known to the skilled persons for molar mass determination, for instance by chromatography such as size exclusion chromatography (SEC, also referred to as gel permeation chromatography, GPC)) in tetrahydrofuran (THF) at 20° C. calibrated with polystyrene standards.

In an embodiment, the mass molar distribution of the copolymers obtained can range between about 1.5 and about 2.16, preferably below 2. Specific $M_w/M_n$ ratios of the copolymers obtained are provided in the tables below.

The process of the present invention allows high conversion of cyclic ester monomer to polycarbonate/polyester copolymer. In an embodiment, the conversion can be of from about 78% to about 100%; preferably, the conversion can be of from about 80% to about 100%. The conversion is calculated as the percentage of monomer converted to copolymer as follows: [amount of precipitated copolymer obtained after the process divided by the amount of cyclic ester as starting material (monomer)]×100. The amount of precipitated copolymer obtained after the process and of cyclic ester as starting material can be measured by weighting. High conversions of cyclic ester monomers to copolymers are reported in the tables below.

The process of the present invention allows improved incorporation of ethylene carbonate monomer into the polyester backbone of the resulting copolymer. In an embodiment, the incorporation of ethylene carbonate can be higher than 4 mol-%; preferably, the incorporation of ethylene carbonate can be of from about 7 mol-% to about 33 mol-%. The incorporation is calculated as the molar percentage (mol-%) of ethylene carbonate monomer converted to copolymer as follows: [molar amount of ethylene carbonate in the precipitated copolymer obtained after the process divided by the sum of the molar amounts of ethylene carbonate and cyclic ester in the precipitated copolymer obtained after the process]×100. The molar amounts of ethylene carbonate and cyclic ester in the precipitated copolymer obtained after the process can be measured by NMR spectroscopy. Improved conversions of ethylene carbonate monomers to copolymers are reported in the tables below at particular operating conditions, employing specific catalytic systems, and specific cyclic esters.

The present invention can be further illustrated by the following examples, although it will be understood that these examples are included merely for purposes of illustration and are not intended to limit the scope of the invention unless otherwise specifically indicated.

EXAMPLES

Comparative Example 1

Failed Copolymerization of Ethyl Carbonate (EC) with ε-Caprolactone (CL) Using Al(OTf)$_3$ The bulk copolymerization of EC and CL ran under the conditions listed in Table 1, revealed the insertion—to some extent (12 mol-%)—of EC in the polyester backbone (Table 1). However, Al(OTf)$_3$ led to complete decarboxylation of the inserted EC units, thus affording the corresponding poly(ester-ether), as revealed by $^1$H and $^{13}$C NMR analyses. The polyethylene oxide segments in this polymer were identified in the $^1$H NMR spectra next to the major signals of PCL, in agreement with literature data (δ 3.3, 3.6 ppm) (Lee J. C., Litt M. H.; Macromolecules, 2000, 33, 1618-1627; Agarwal S., Naumann N., Xie X.; Macromolecules, 2002, 35, 7713-7717). FIG. 1 illustrates the $^1$H NMR spectrum (CDCl$_3$, 400 MHz, 23° C.) of the polymer recovered from the copolymerization of EC and CL (Table 1 below, entry 1).

Correspondingly, the $^{13}$C{$^1$H} NMR spectrum of the polymer recovered from the copolymerization of EC and CL using Al(OTf)$_3$ as catalyst did not show the signal of the expected carbonyl group of the carbonate units (δ ca. 155.0-155.4 ppm), next to the EC monomer singlet (δ 155.5 ppm). However, peaks corresponding to the enchainment of a CL and decarboxylated-EC (ether) consecutive units were clearly observed (δ 70.8 ppm).

Figure 2:
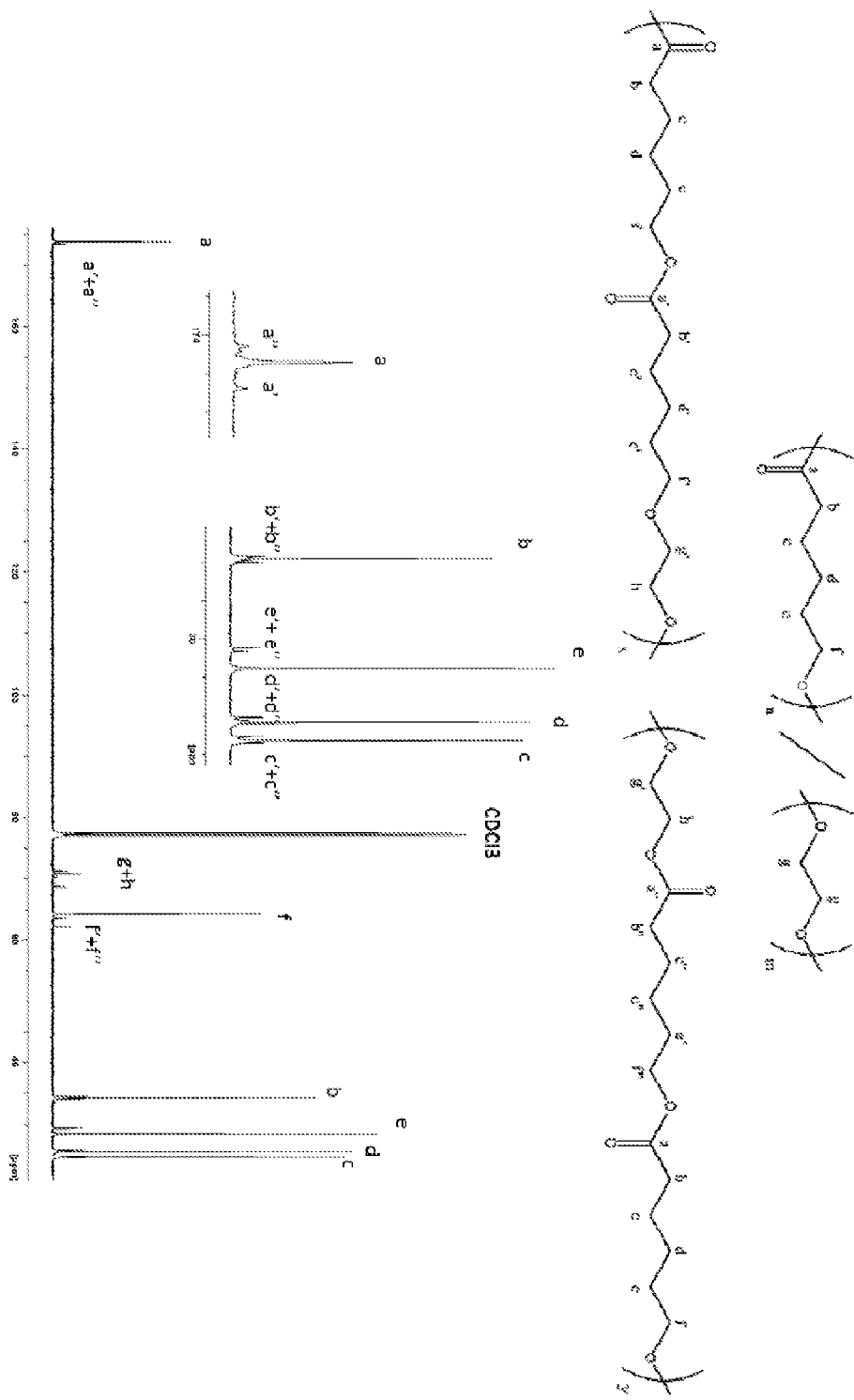
FIG. 2 illustrates the $^{13}$C{$^1$H} NMR spectrum (CDCl$_3$, 100 MHz, 23° C.) of the polymer recovered from the copolymerization of EC and CL (Table 1) and relating to comparative Example 1.

FIG. 2 illustrates the $^{13}$C{$^1$H} NMR spectrum (CDCl$_3$, 100 MHz, 23° C.) of the polymer recovered from the copolymerization of EC and CL (Table 1) and assignments.

Example 2

Copolymerization of Ethyl Carbonate (EC) with β-Butyrolactone (BL)

The copolymerization of EC and BL was performed using the following catalytic systems: Al(OTf)$_3$, the β-diiminate complex developed by Coates [(BDI)Zn(NTMS$_2$)] (Chamberlain B. M., Cheng M., Moore D. R., Ovitt T. M., Lobkovsky E. B., Coates G. W.; J. Am; Chem. Soc., 2001, 123, 3229-3230), and the diaminophenolate zinc complex developed by Tolman, [(NNO)ZnEt](Williams C. K., Breyfogle L. E., Choi S. K., Nam W., Young V. G., Hillmeyer M. A., Tolman W. B.; J. Am. Chem. Soc., 2003, 125, 11350-11359). These metallic species were combined to an exogenous protic source, typically an alcohol (benzyl alcohol, BnOH), used in excess, acting both as initiator and transfer agent, so as to operate in an "immortal" ROP approach. A [catalyst]$_0$/[BnOH]$_0$ ratio of 1:5 was used in the present example.

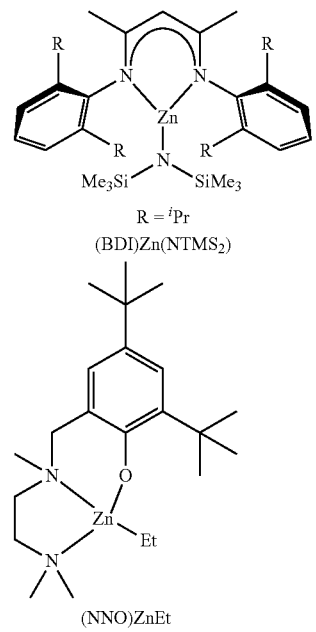

Copolymerization Procedure

In a glovebox, Tolman's zinc complex [(NNO)ZnEt](5.0 mg, 0.012 mmol) was added to a Schlenk flask prior to the addition of EC (257 mg, 2.92 mmol). BL (503 mg, 5.84

TABLE 1

Results of the EC and CL copolymerization catalyzed by Al(OTf)$_3$

| Entry | [EC]$_0$:[ε-CL]$_0$:[Al(OTf)$_3$]$_0$:[BnOH]$_0$ | Temp (° C.) | Solvent | Time (h) | EC Conv. (%) | ε-CL Conv. (%) | mol-% EC in copolymer | Mn$_{sec}$ | M$_w$/M$_n$ |
|---|---|---|---|---|---|---|---|---|---|
| 1 | 250:500:1:2.5 | 110 | — | 15 | total decarboxylation | 100 | Only ether units | nd | nd | mmol) was then added to the mixture using a syringe. The mixture was stirred under argon at 60° C. over an appropriated time period.

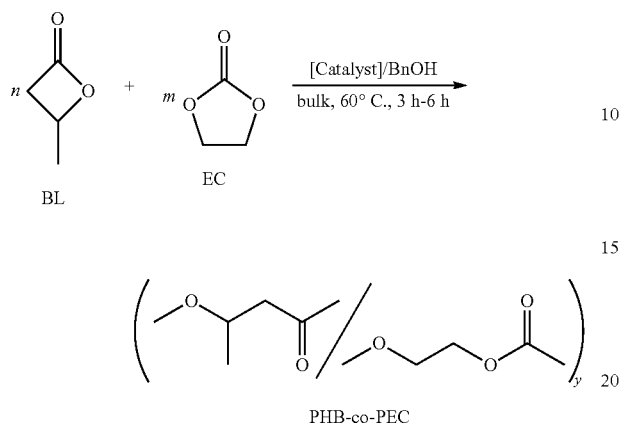

PHB-co-PEC

Synthesis of PHB-co-PEC by Simultaneous Copolymerization of EC and BL

Determination of the EC Content in the Copolymer by $^1$H NMR Analysis

The copolymers were then characterized by $^1$H and $^{13}$C NMR and SEC (as well as DSC for some of them) analyses. The molar mass and molar mass distribution values of the copolymers were determined by SEC in THF. The values reported in Table 2 below were determined against polystyrene standards and were uncorrected for any difference in hydrodynamic radius.

The EC molar content values were determined by $^1$H NMR spectroscopy analysis from the relative intensity of the signals of the methine hydrogens of the BL chains (CH$_2$(CH$_3$)CHOC(O)—, δ=5.13-5.25 ppm) and the relative intensity of the methylene hydrogens of the EC units ((O)COCH$_2$CH$_2$OC(O)—, δ=4.29 ppm)

mol-% of inserted EC. Tolman's zinc complex [(NNO)ZnEt] operated either in presence (iROP) or absence (ROP) of added alcohol. When used in absence of alcohol, it enabled to copolymerize EC and BL at 60° C., in bulk or in toluene solution, with quite good efficiency. Up to 26 mol-% of EC could be incorporated in the copolymer. Copolymers of relatively high molar mass (Mn$_{SEC}$=34,400 g·mol$^{-1}$) with Mw/Mn<1.6 could thus be prepared. Among the three catalytic systems evaluated, the one based on Tolman's zinc complex, operating at a lower temperature, thus gave the best performances for the copolymerization of EC and BL (Table 2).

Figure 3:
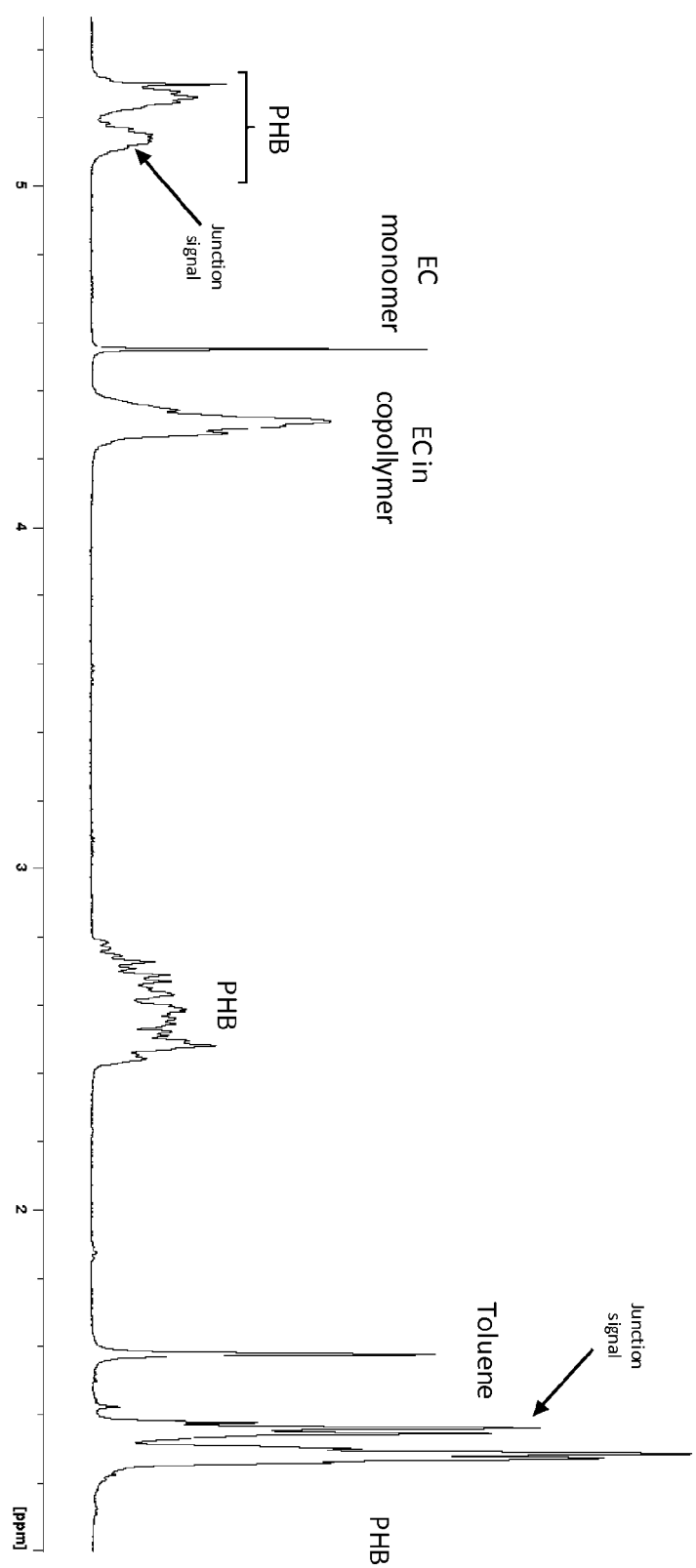
FIG. 3 illustrates the $^1$H NMR spectrum (CDCl$_3$, 400 MHz, 23° C.) of the polymer recovered from the copolymerization of EC and β-butyrolactone (BL) (Table 2, entry 4) of Example 2.

FIG. 3 illustrates the $^1$H NMR spectrum (CDCl$_3$, 400 MHz, 23° C.) of the polymer recovered from the copolymerization of EC and β-butyrolactone (BL) (Table 2, entry 4).

Example 3

Copolymerization of Ethyl Carbonate (EC) with ε-Caprolactone (CL)

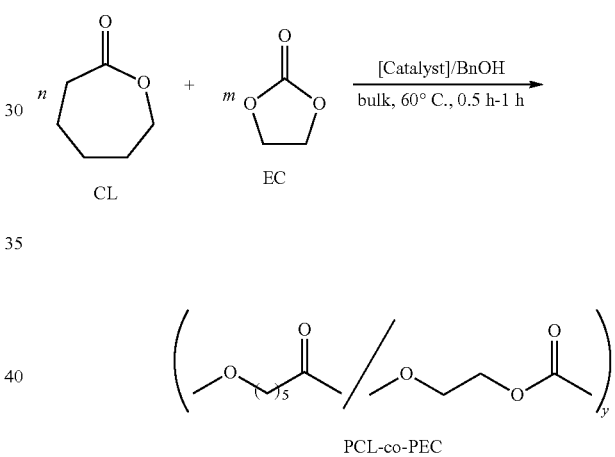

PCL-co-PEC

TABLE 2

Results of the EC and BL simultaneous copolymerization promoted by different catalytic systems

| Entry | Catalyst | [EC]$_0$:[BL]$_0$:[catalyst]$_0$:[BnOH]$_0$ | Temp (° C.) | Solvent | Time (h) | EC Conv. (%) | BL Conv. (%) | mol-% EC in copolymer | Mn$_{sec}$ | M$_w$/M$_n$ |
|---|---|---|---|---|---|---|---|---|---|---|
| 1 | Al(OTf)$_3$ | 200:400:1:5 | 110 | — | 5 | 27 (decarboxylation) | 92 | nd | nd | nd |
| 2 | [(BDI)Zn(NTMS$_2$)] | 165:500:1:5 | 80 | — | 6.25 | nd | nd | 15 | nd | nd |
| 3 | [(BDI)Zn(NTMS$_2$)] | 250:500:1:5 | 90 | — | 3.5 | 25 | 95 | 18 | 6000 | 1.29 |
| 4 | (NNO)ZnEt | 250:500:1:0 | 60 | — | 5 | 33 | 81 | 26 | 17350 | 1.56 |
| 5 | (NNO)ZnEt | 250:500:1:0 | 60 | Toluene [2M] | 6 | 44 | 97 | 21 | 34400 | 1.62 |

Copolymerization catalyzed by aluminum triflate/BnOH at 110° C. led to decarboxylation of the EC units, as previously observed for the copolymerization of EC and CL. The catalytic system derived from the zinc β-diiminate appeared effective at high temperature, typically at 90° C., allowing almost all the BL to be polymerized and affording up to 18

Synthesis of PCL-co-PEC by Simultaneous Copolymerization of EC and CL

Different reactions were performed by using the catalyst Tolman's zinc complex [(NNO)ZnEt] or Al(OTf)$_3$, which were added to a Schlenk flask prior to the addition of EC. CL was then added to the mixture. The mixture was allowed to react at the operating conditions depicted in Table 3 below.

TABLE 3

Results of the EC and CL copolymerization reactions catalyzed by different systems in bulk

| Entry | Catalyst | $[EC]_0$:$[CL]_0$:$[catalyst]_0$:$[BnOH]_0$ | Temp (°C.) | Solvent | Time (h) | EC Conv. (%) | CL Conv. (%) | mol-% EC in copolymer | $Mn_{sec}$ | $M_w/M_n$ |
|---|---|---|---|---|---|---|---|---|---|---|
| 1 | Al(OTf)$_3$ | 250:500:1:2.5 | 110 | — | 15 | total decarboxylation | 100 | nd | nd | nd |
| 2 | (NNO)ZnEt | 125:250:1 | 60 | — | 4 | 27 | 100 | 14 | 28700 | 1.59 |
| 3 | (NNO)ZnEt | 250:250:1 | 60 | — | 0.5 | 30 | 84 | 28 | 50731 | 1.64 |
| 4 | (NNO)ZnEt | 500:250:1 | 60 | — | 1 | 20 | 85 | 33 | 37535 | 1.65 |

Complete decarboxylation was observed when EC and CL were copolymerized by Al(OTf)$_3$ at 110° C. Similarly to its behavior in EC/BL copolymerization, the catalytic system based on Zn-Tolman complex, [(NNO]ZnEt], gave unprecedented and promising results in the copolymerization of EC and CL. Within 30 minutes at 60° C., for a molar feed ratio of 50:50 (EC/CL), up to 33 mol-% of EC was successfully inserted in PCL. The activities (TOF=150 mol$_{EC}$·mol$_{cata}$·h$^{-1}$) and productivities (TON$_{EC}$=100 in 1 h) obtained were quite good for this kind of copolymerization. By increasing the molar feed ratio the final EC content was increased from 14 mol-% for a ratio of 33:66 (EC/CL) to 33 mol-% for a ratio

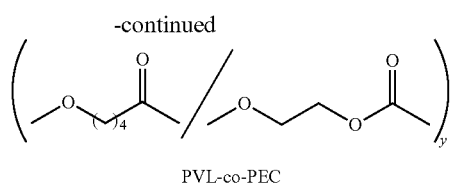

PVL-co-PEC

Synthesis of PCL-co-PEC by Simultaneous Copolymerization of EC and VL

The copolymerization between EC and δ-valerolactone (VL) promoted by the Zn-Tolman catalytic system gave a similar result, as shown in Table 4. A significant insertion (25 mol-%) of EC in the VL backbone, within a relatively short time period (1 h), was obtained.

TABLE 4

Result of the EC and VL copolymerization reactions catalyzed by Tolman's zinc complex

| Entry | $[EC]_0$:$[δ-VL]_0$:$[Zn Tolman]_0$ | Temp (°C.) | Solvent | Time (h) | Conv. EC (%) | Conv. δ-VL (%) | mol-% EC in copolymer | $Mn_{sec}$ | $M_w/M_n$ |
|---|---|---|---|---|---|---|---|---|---|
| 1 | 125:250:1 | 60 | — | 1 | 38 | 78 | 13 | nd | nd | nd: not determined

66:33 (EC/CL). NMR analyses (FIGS. 4, 5) of the recovered polymers revealed the presence of EC-EC homo-sequences.

Figure 4:
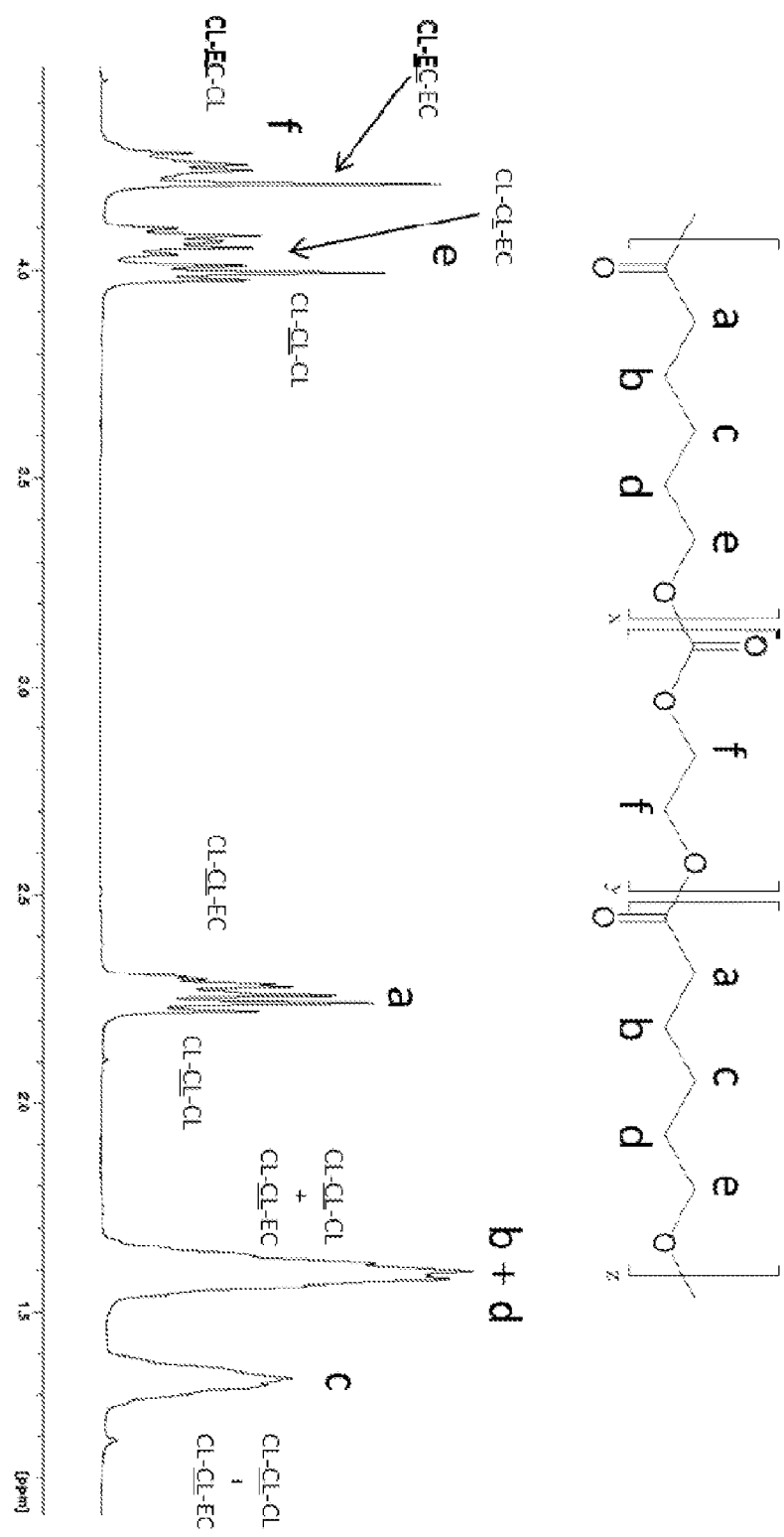
FIG. 4 illustrates the $^1$H NMR spectrum (CDCl$_3$, 400 MHz, 23° C.) of the polymer recovered from the copolymerization of EC and CL with [(NNO]ZnEt] as catalyst (Table 3, entry 4) and relating to Example 3.

FIG. 4 illustrates the $^1$H NMR spectrum (CDCl$_3$, 400 MHz, 23° C.) of the polymer recovered from the copolymerization of EC and CL (Table 3, entry 4)

Figure 5:
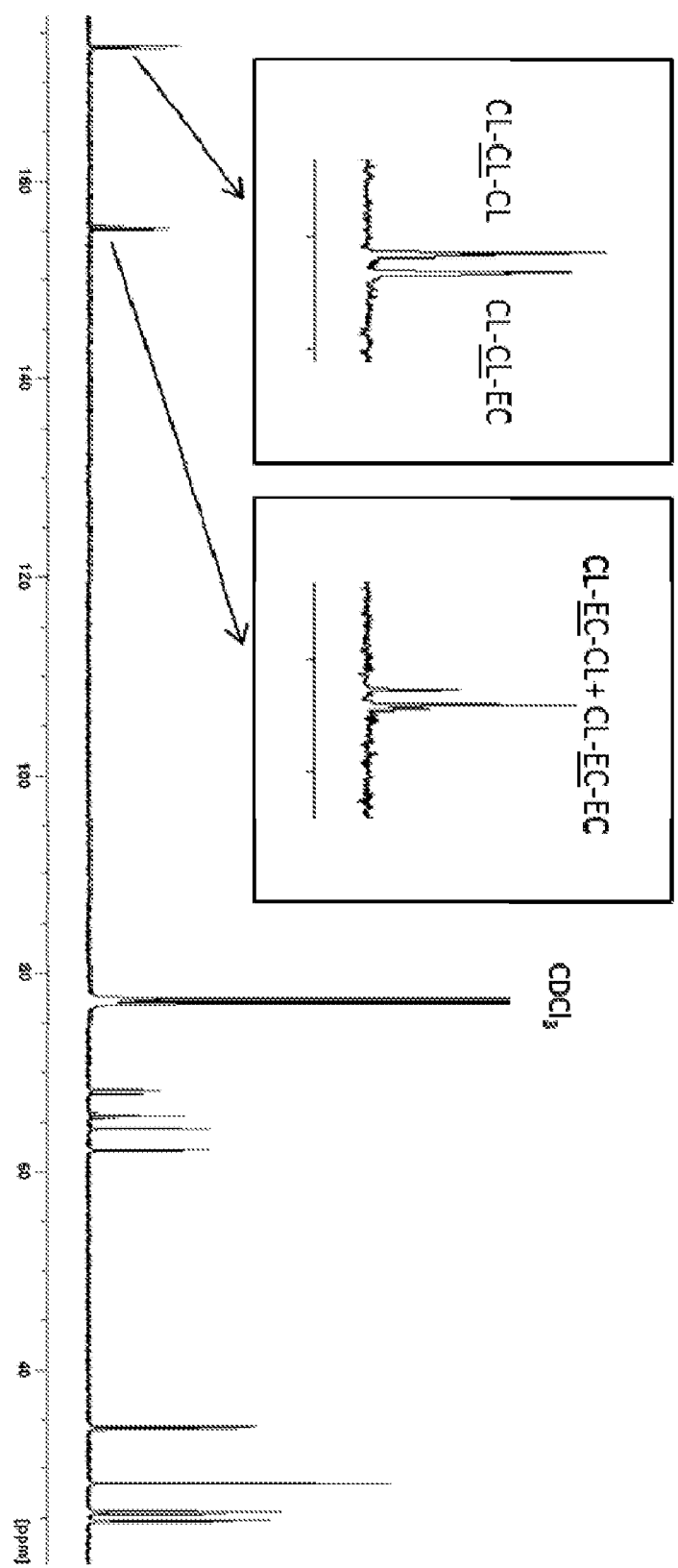
FIG. 5 illustrates the $^{13}$C{$^1$H} NMR spectrum (CDCl$_3$, 100 MHz, 23° C.) of the polymer recovered from the copolymerization of EC and CL with [(NNO]ZnEt] as catalyst (Table 3, entry 4) and relating to Example 3.

FIG. 5 illustrates the $^{13}$C NMR spectrum (CDCl$_3$, 400 MHz, 23° C.) of the polymer recovered from the copolymerization of EC and CL (Table 3, entry 4)

The $^{13}$C{$^1$H} NMR spectra (FIG. 5) clearly display two signals around δ 155 ppm assigned to the hetero-sequences CL-EC-CL and homo-sequences CL-EC-EC.

Example 4

Copolymerization of Ethyl Carbonate with δ-Valerolactone

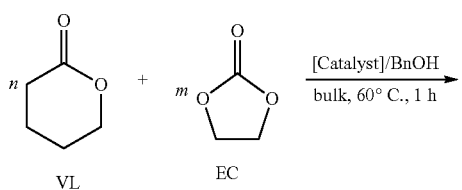

Figure 6:
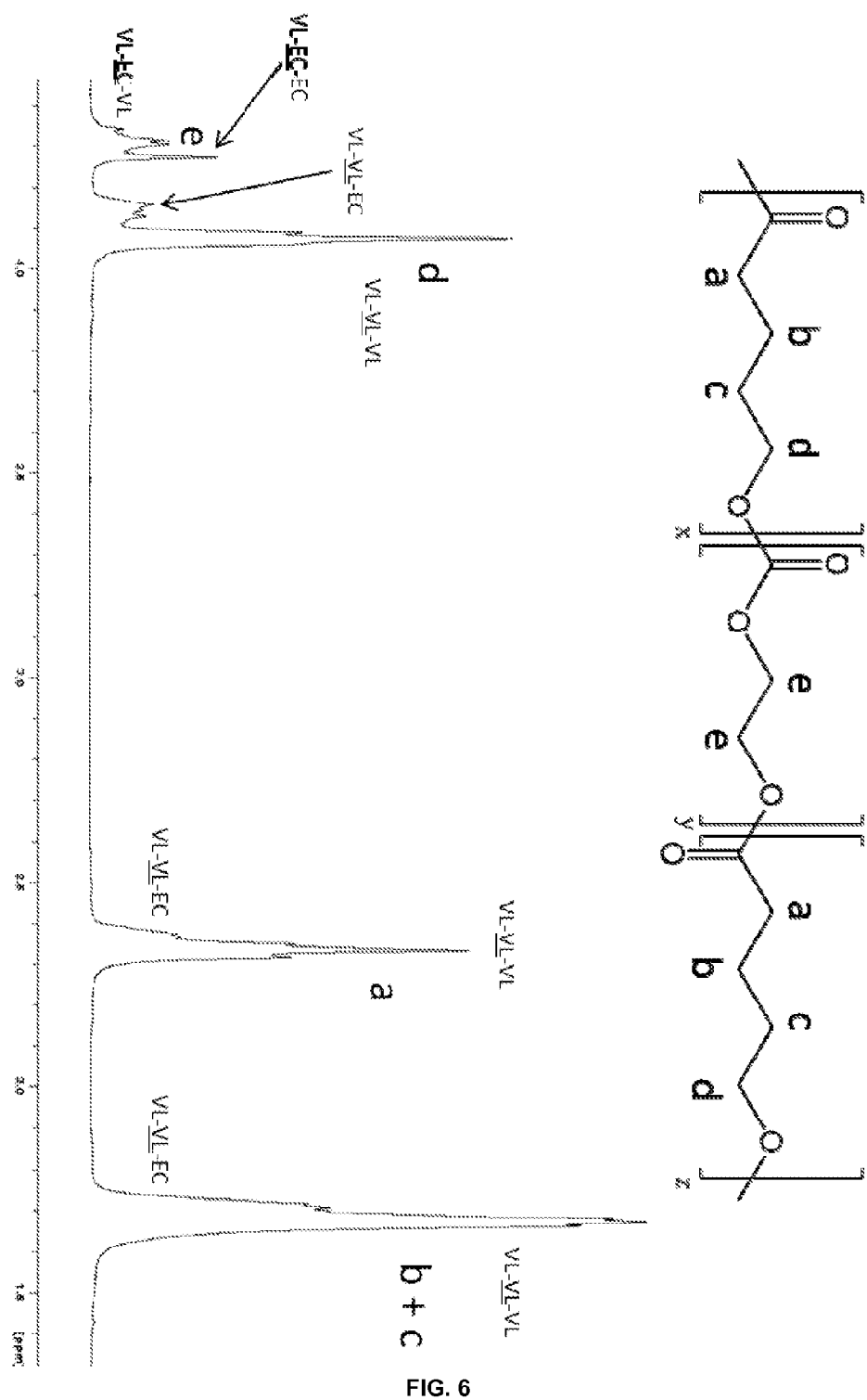
FIG. 6 illustrates the $^1$H NMR spectrum (CDCl$_3$, 400 MHz, 23° C.) of the polymer recovered from the copolymerization of EC and δ-valerolactone (VL) with [(NNO]ZnEt] as catalyst (Table 4, entry 1) and relating to Example 4.

FIG. 6 illustrates the $^1$H NMR spectrum (CDCl$_3$, 400 MHz, 23° C.) of the polymer recovered from the copolymerization of EC and VL (Table 4, entry 1)

Figure 7:
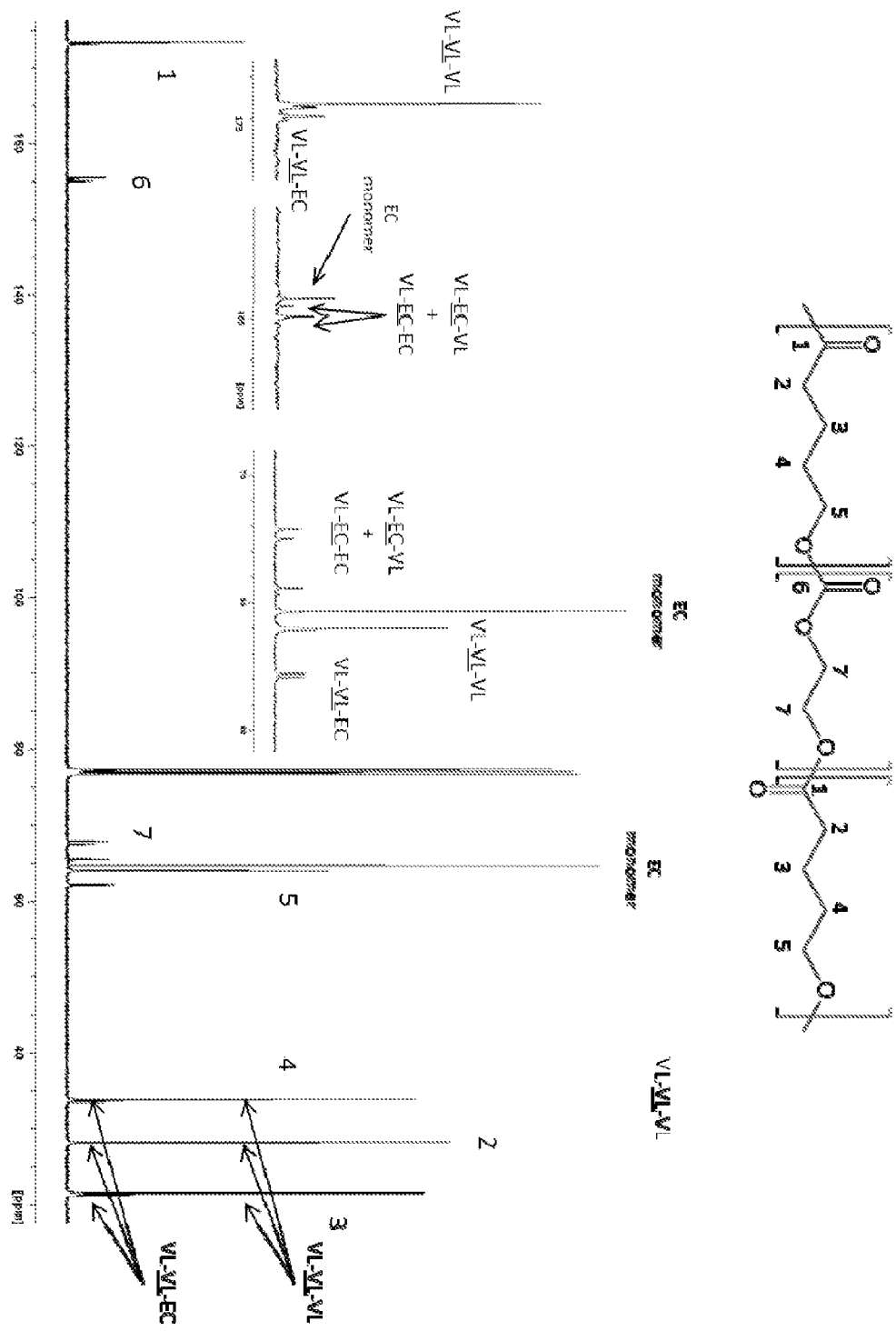
FIG. 7 illustrates the $^{13}$C{$^1$H} NMR spectrum (CDCl$_3$, 100 MHz, 23° C.) of the polymer recovered from the copolymerization of EC and VL with (NNO)ZnEt as catalyst (Table 4, entry 1) and relating to Example 4; signals due to residual EC monomer are observed.

FIG. 7 illustrates the $^{13}$C NMR spectrum (CDCl$_3$, 400 MHz, 23° C.) of the polymer recovered from the copolymerization of EC and VL (Table 4, entry 1)

The NMR analyses show also the presence of two signals in the $^{13}$C NMR spectra (FIG. 7), one corresponding to the CL$_x$-EC$_y$ homosequences and the other to CL-EC-CL heterosequences.

Example 5

Copolymerization of Ethyl Carbonate (EC) with L-Lactide (LA)

Copolymerization was performed using the catalytic system Zn-Tolman complex, [(NNO]ZnEt], which led to insertion of EC (from 7 to 17 mol-%) in the PLA backbone. The results are shown in Tables 5, 6, and 7.

TABLE 5

Results of the EC and L-LA copolymerization reactions catalyzed by zinc complexes

| Entry | catalyst | [EC]$_0$:[L-LA]$_0$:[catalyst]$_0$ | Temp (° C.) | Solvent | Time (h) | EC Conv. (%) | L-LA Conv. (%) | EC in copolymer (mol-%) | Mn$_{sec}$ | M$_w$/M$_n$ |
|---|---|---|---|---|---|---|---|---|---|---|
| 1 | (NNO)ZnEt | 160:160:1 | 60 | Toluene [4M] | 1 | 4 | 97 | 1 | nd | nd |
| 2 | (NNO)ZnEt | 160:160:1 | 60 | — | 0.5 | 4 | 95 | 2 | nd | nd |
| 3 | (NNO)ZnEt | 100:500:1 | 100 | — | 0.5 | nd | nd | 1.5 | 96350 | 2.16 |
| 4 | (NNO)ZnEt | 100:500:1 | 100 | — | 0.5 | nd | nd | 4 | 56900 | 2.15 |
| 5 | (NNO)ZnEt | 150:150:1 | 100 | — | 0.2 | 6 | 94 | 7 | nd | tbd |
| 6 | (NNO)ZnEt | 250:100:1 | 100 | — | 0.5 | 6 | 96 | 9 | 18622 | 1.6 |
| 7 | (NNO)ZnEt | 500:100:1 | 60 | — | 1 | 1 | 85 | 3 | 78100 | 1.85 |
| 8 | (NNO)ZnEt | 500:100:1 | 80 | — | 1.5 | 3 | 94 | 13 | 48300 | 1.59 |
| 9 | (NNO)ZnEt | 500:100:1 | 100 | — | 1 | nd | nd | 13 | 45800 | 1.53 |
| 10 | (NNO)ZnEt | 500:100:1 | 100 | — | 2.5 | 7 | 90 | 17 | 29500 | 1.73 |
| 11 | (NNO)ZnEt | 500:100:1 | 120 | — | 1 | 4 | 90 | 14 | 19400 | 1.5 |
| 12 | (NNO)ZnEt | 500:100:1 | 150 | — | 3 | 3 | 83 | unprecipitable | — | — |
| 13 | (NNO)ZnEt | 500:100:1 | 150 | — | 1 | 2 | 80 | unprecipitable | — | — |
| 14 | (NNO)ZnEt | 2500:500:1 | 100 | — | 3 | 4 | 90 | 11 | 60160 | 1.74 |
| 15 | (NNO)ZnEt | 1500:1500:1 | 100 | — | | | | On going | | |
| 16 | (NNO)ZnEt | 500:2500:1 | 100 | — | | | | On going | | |
| 17 | [(BDI)Zn(NTMS$_2$)] | 500:100:1 | 100 | — | 1 | 2 | 90 | 5 | nd | nd |
| 18 | (NNO)ZnEt/BnOH | 500:100:1:5 | 100 | — | 1 | 7 | 92 | unprecipitable | — | — | nd: not determined

With Tolman's zinc complex [(NNO)ZnEt], increasing the reaction temperature from 60° C. to 100° C. allowed to increase the insertion of EC units from 2 mol-% to 7 mol-% (Table 5, entry 2 vs 5).

TABLE 6

Influence of the temperature on the LA/EC copolymerization with Tolman's zinc catalyst

| Entry | Catalyst | [EC]$_0$:[L-LA]$_0$:[Catalyst]$_0$ | ratio | Temp (° C.) | Solvent | Time (h) | Conv. EC (%) | Conv. L-LA (%) | EC in copolymer (%) | Mn$_{sec}$ | M$_w$/M$_n$ |
|---|---|---|---|---|---|---|---|---|---|---|---|
| 1 | (NNO)ZnEt | 500:100:1 | 83/17 | 60 | — | 1 | 1 | 85 | 3 | 78097 | 1.85 |
| 2 | (NNO)ZnEt | 500:100:1 | 83/17 | 80 | — | 1.5 | 3 | 94 | 13 | 48307 | 1.59 |
| 3 | (NNO)ZnEt | 500:100:1 | 83/17 | 100 | — | 1 | nd | nd | 13 | 45800 | 1.53 |
| 4 | (NNO)ZnEt | 500:100:1 | 83/17 | 120 | — | 1 | 4 | 90 | 14 | 19422 | 1.5 |
| 5 | (NNO)ZnEt | 500:100:1 | 83/17 | 150 | — | 1 | 2 | 80 | unprecipitable | — | — |

TABLE 7

Influence of the feed ratio on the LA/EC copolymerization with Tolman's zinc catalyst.

| Entry | Catalyst | [EC]$_0$:[L-LA]$_0$:[Catalyst]$_0$ | ratio | Temp (° C.) | Solvent | Time (h) | Conv. EC (%) | Conv. L-LA (%) | EC in copolymer (mol-%) | Mn$_{sec}$ | M$_w$/M$_n$ |
|---|---|---|---|---|---|---|---|---|---|---|---|
| 1 | (NNO)ZnEt | 500:100:1 | 83/17 | 100 | — | 2.5 | 6 | 90 | 17 | 29500 | 1.73 |
| 2 | (NNO)ZnEt | 250:100:1 | 71/29 | 100 | — | 0.5 | 6 | 96 | 9 | 18622 | 1.6 |
| 3 | (NNO)ZnEt | 150:150:1 | 50/50 | 100 | — | 0.2 | 6 | 94 | 7 | nd | nd |
| 4 | (NNO)ZnEt | 100:250:1 | 29/71 | 100 | — | 0.5 | nd | nd | 4 | 56879 | 2.15 |
| 5 | (NNO)ZnEt | 100:500:1 | 17/83 | 100 | — | 0.5 | nd | nd | 1.5 | 96355 | 2.16 | nd: not determined

LLA-EC copolymers with molar mass values up to 96,350 g·mol$^{-1}$ (vs Mn$_{th}$=80,800 g·mol$^{-1}$) with molar mass distribution values generally <2.0 could be obtained.

Figure 8:
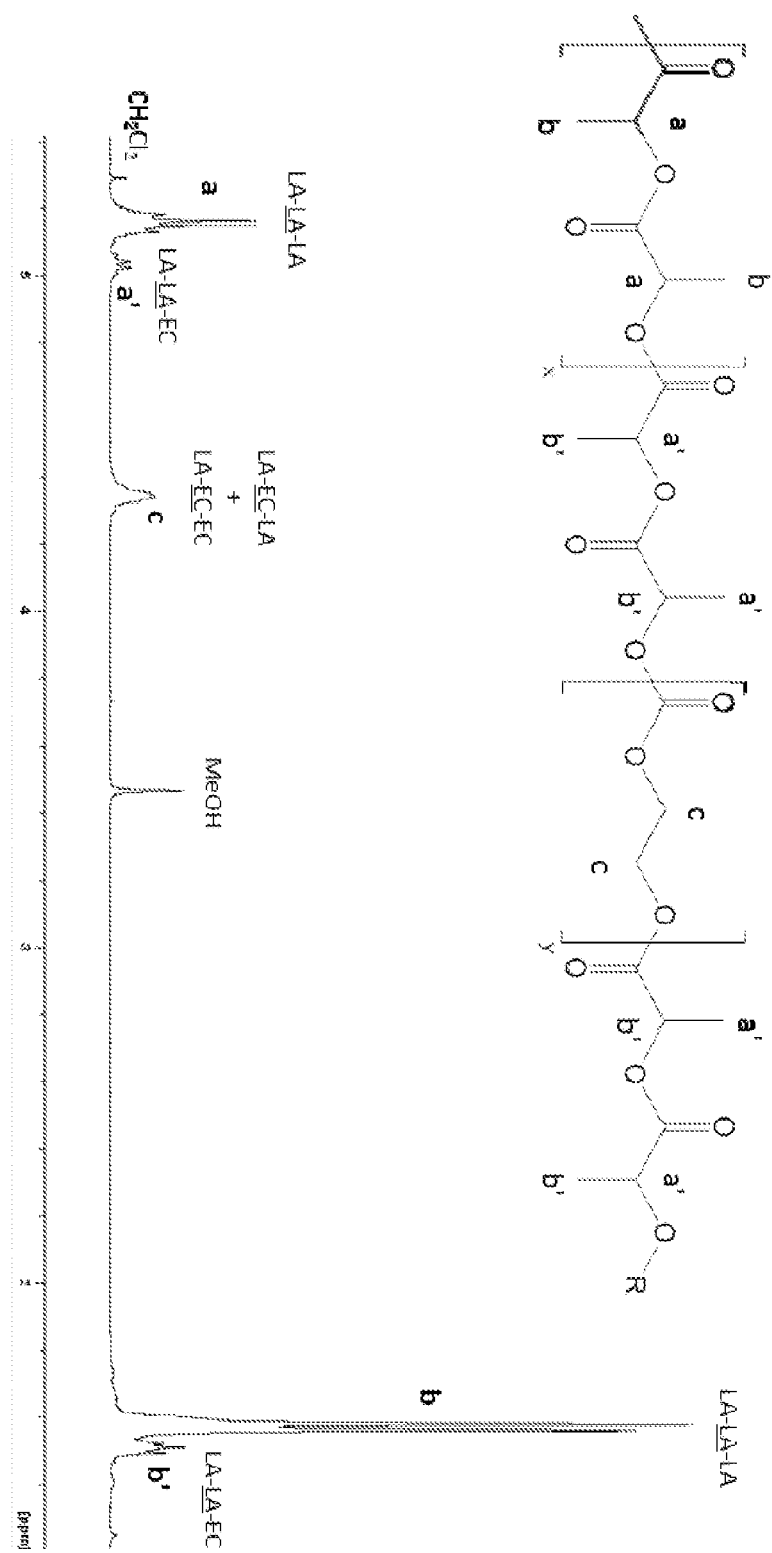
FIG. 8 illustrates the $^1$H NMR spectrum (CDCl$_3$, 400 MHz, 23° C.) of the polymer recovered from the copolymerization of EC and LA reaction with [(NNO)ZnEt] as catalyst (Table 5, entry 10) and relating to Example 5.

In FIG. 8 there is illustrated the $^1$H NMR spectrum (CDCl$_3$, 400 MHz, 23° C.) of the polymer recovered from the copolymerization of EC and LA reaction with (NNO)ZnEt as catalyst (Table 5, entry 10).

Figure 9:
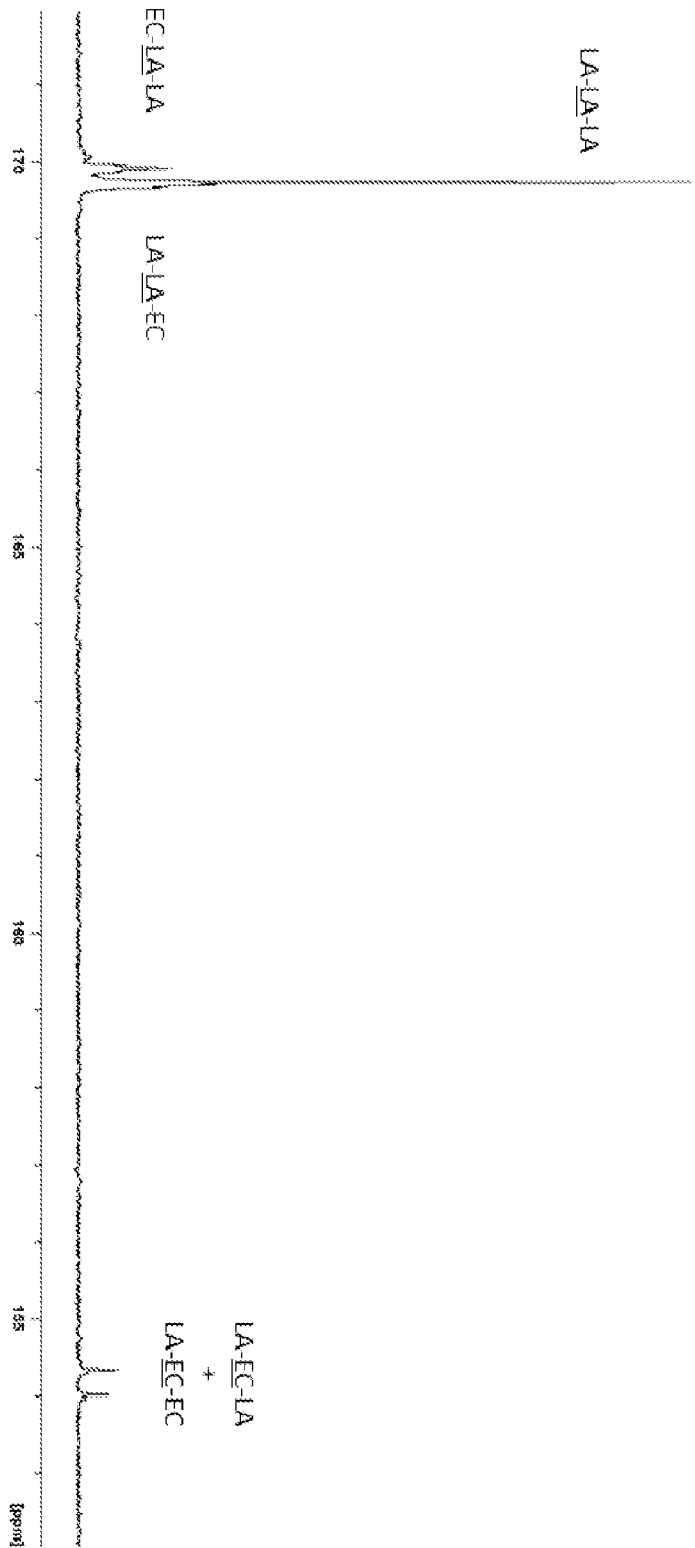
FIG. 9 illustrates the $^{13}$C{$^1$H} NMR spectrum (CDCl$_3$, 100 MHz, 23° C.) of the polymer recovered from the copolymerization of EC and lactide (LA) with [(NNO)ZnEt] as catalyst (Table 5, entry 10) and relating to Example 5.

In FIG. 9 there is illustrated the $^{13}$C{$^1$H} NMR spectrum (CDCl$_3$, 100 MHz, 23° C.) of the polymer recovered from the copolymerization of EC and LA with (NNO)ZnEt as catalyst (Table 5, entry 10) and proposed assignments.

The $^{13}$C{$^1$H} NMR spectrum of the copolymer obtained from the copolymerization of EC and LLA (Table 5, entry 10,) shows the presence of two signals corresponding to the carbonate in (FIG. 9). This may arise from the presence of hetero- and homosequences of ethylene carbonate in the copolymer.

DSC analysis of the sample obtained from experiment (Table 5, entry 5) shows a Tg=53° C. and a Tm=149° C. (for PLLA Tg=65° C. and Tm=175° C.). Thus, the insertion of EC into a PLLA backbone affects the thermal properties of PLLA.

The invention claimed is:

1. A process for copolymerizing i) ethylene carbonate with ii) one or more cyclic esters, comprising contacting the ethylene carbonate with the one or more cyclic esters in the presence of one or more catalysts of formula (I) or (II),

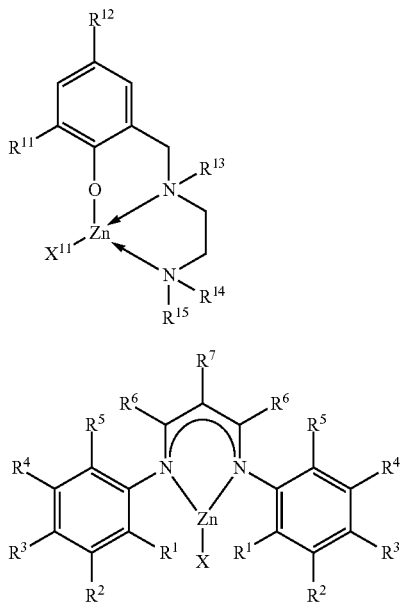

wherein $R^1$, $R^2$, $R^3$, $R^4$, $R^5$, $R^6$, and $R^7$ are each independently selected from the group consisting of hydrogen, optionally substituted $C_{1-12}$alkyl, and an inert functional group, and wherein two or more of said groups are optionally linked together to form one or more rings;

wherein X is —N(SiR$^{27}_3$)$_2$, $C_{1-12}$alkyl, $C_{1-12}$alkoxy, —NR$^9$R$^{10}$ or —BH$_4$, and each R$^{27}$ is independently selected from hydrogen and $C_{1-6}$alkyl;

wherein each R$^9$ and R$^{10}$ is independently selected from hydrogen and $C_{1-6}$alkyl;

wherein R$^{11}$ and R$^{12}$ are each independently $C_{1-10}$alkyl;

wherein R$^{13}$, R$^{14}$, and R$^{15}$ are each independently $C_{1-10}$alkyl, or wherein R$^{13}$ and R$^{14}$ are covalently bound to each other and are each a methylene and R$^{15}$ is $C_{1-10}$alkyl, wherein X$^{11}$ is selected from $C_{1-10}$alkyl, —OR$^{16}$, and —N(SiR$^{17}_3$)$_2$;

wherein R$^{16}$ is $C_{1-10}$alkyl; and wherein each R$^{17}$ is independently selected from hydrogen and $C_{1-6}$alkyl.

2. The process according to claim 1, wherein R$^{11}$ and R$^{12}$ are each independently $C_{1-6}$alkyl.

3. The process according to claim 1, wherein R$^{13}$, R$^{14}$ and R$^{15}$ are each independently $C_{1-6}$alkyl.

4. The process according to claim 1, wherein X$^{11}$ is selected from $C_{1-6}$alkyl, —OR$^{16}$, or —N(SiR$^{17}_3$)$_2$, R$^{16}$ is $C_{1-6}$alkyl, and each R$^{17}$ is independently selected from hydrogen and $C_{1-4}$alkyl.

5. The process according to claim 1, wherein the one or more catalysts are selected from [(NNO)ZnEt], [BDI]Zn(N(SiMe$_3$)$_2$), [BDI]Zn(Et) and {[BDI]Zn(OR$^{30}$)}$_2$ wherein R$^{30}$ is $C_{1-6}$alkyl.

6. The process according to claim 1, wherein the process is performed in the presence of a compound of formula (III), acting as a co-initiator and transfer agent of the polymerization, $$R^8\text{—OH} \qquad (III)$$

wherein R$^8$ is selected from the group consisting of $C_{1-20}$alkyl, $C_{6-30}$aryl, and $C_{6-30}$aryl $C_{1-20}$alkyl optionally substituted by one or more substituents selected from the group consisting of halogen, hydroxyl, and $C_{1-6}$alkyl.

7. The process according to claim 6, wherein the compound of formula (III) is 1-octanol, isopropanol, propanediol, trimethylolpropane, 2-butanol, 3-buten-2-ol, 1,3-butanediol, 1,4-butanediol, 1,6-hexanediol, 1,7-heptanediol, benzyl alcohol, 4-bromophenol,1,4-benzenedimethanol, and (4-trifluoromethyl)benzyl alcohol.

8. The process according to claim 1, wherein the one or more cyclic esters are selected from the group consisting of glycolide, lactide, β-butyrolactone, δ-valerolactone, and ε-caprolactone.

9. The process according to claim 1, wherein the process is performed with or without solvent.

10. The process according to claim 9, wherein the process is performed with solvent, and wherein the solvent is selected from an aliphatic or aromatic hydrocarbon, an ether or an halogenated solvent.

11. The process according to claim 1, wherein the process is performed in bulk.

12. The process according to claim 1, wherein the process is performed with a lactone selected from the group consisting of β-butyrolactone, δ-valerolactone, and ε-caprolactone, in the presence of a solvent and at a temperature of at least 60° C. and at most 110° C.

13. The process according to claim 1, wherein the process is performed with a lactone selected from the group consisting of β-butyrolactone, δ-valerolactone, and ε-caprolactone, in bulk and at a temperature of at least 60° C. and at most 80° C.

14. The process according to claim 1, wherein the process is performed with glycolide or a lactide and at a temperature of at least 60° C. and at most 120° C.

15. The process according to claim 1, wherein the copolymer prepared is an ether-free polyethylenecarbonate/polyester copolymer.

16. The process according to claim 1, wherein the one or more catalysts comprise [(NNO)ZnEt], having the structure:

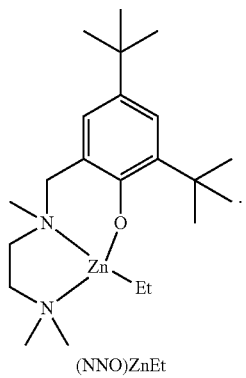

(NNO)ZnEt

17. The process according to claim 1, wherein the one or more catalysts comprise:
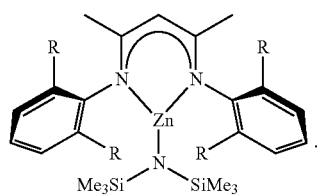
$R = {}^i Pr$
(BDI)Zn(NTMS$_2$)
* * * * *